United States Patent [19]

Suzuki

[11] 4,200,607
[45] Apr. 29, 1980

[54] AUTOMATIC CHEMICAL ANALYZER

[75] Inventor: Nobuyoshi Suzuki, Hachioji, Japan

[73] Assignee: Olympus Opitcal Co., Ltd., Tokyo, Japan

[21] Appl. No.: 949,771

[22] Filed: Oct. 10, 1978

[30] Foreign Application Priority Data

Nov. 21, 1977 [JP] Japan .................. 52/139764

[51] Int. Cl.² .................. G01N 21/24; G01N 1/14
[52] U.S. Cl. .................. 422/64; 422/81
[58] Field of Search .......... 422/64, 63, 65, 66, 422/67, 81; 141/130

[56] References Cited

U.S. PATENT DOCUMENTS

| | | | |
|---|---|---|---|
| 3,592,605 | 7/1971 | Noma et al. | 422/64 |
| 3,762,879 | 10/1973 | Moran | 422/67 |
| 3,799,744 | 3/1974 | Jones | 422/65 |
| 3,881,872 | 5/1975 | Naono | 422/64 |
| 4,052,161 | 10/1977 | Atwood et al. | 422/64 |
| 4,054,416 | 10/1977 | Duff | 422/64 |
| 4,158,545 | 6/1979 | Yamashita et al. | 422/67 |

Primary Examiner—R. E. Serwin
Attorney, Agent, or Firm—Ostrolenk, Faber, Gerb & Soffen

[57] ABSTRACT

An automatic chemical analyzer includes a rotary disc which is intermittently driven for rotation in a given direction and which is provided with a plurality of holders, each of which receives a reaction tube therein. The reaction tubes are disposed to move through an annular channel of a thermostat liquid vessel which maintains first reagent and a liquid sample to be examined, both injected into a reaction tube, at a given temperature. Second reagent is heated to a predetermined temperature before it is injected into the reaction tube. After the injection, the liquids are agitated to mix them together, and the resulting reaction solution is then subject to a colorimetric determination by an optical measuring instrument. Subsequently, the reaction solution is discarded, and rinse water which is previously heated to a given temperature is supplied to the tube for cleaning it.

11 Claims, 8 Drawing Figures

FIG. I (PRIOR ART)

AUTOMATIC CHEMICAL ANALYZER

BACKGROUND OF THE INVENTION

The invention relates to an automatic chemical analyzer, and more particularly, to an improvement of such apparatus which performs the analysis of liquid sample such as blood or the determination of enzyme automatically.

Recently, there has been developed an automatic chemical analyzer which performs the analysis of liquid sample such as blood or urine or the determination of enzyme activity in an accurate, rapid and automatic manner. Such apparatus finds an extensive application in the field of clinical, chemical and pharmaceutical arts. The apparatus comprises means for injecting a liquid sample or reagent into a reaction tube, means which provides a colorimetric determination of the liquid after the chemical reaction or in the process thereof, and means for cleaning the tube with a flow of cleaning liquid through the tube after the reaction solution has been discharged from the tube upon completion of the determination. The apparatus is arranged to achieve an automatic analysis of a number of liquid samples to be examined in sequence in accordance with specified examining items.

While the reaction tube is maintained at a given temperature, for example, 37° C., which is required for the determination, reagent or cleaning liquid which is injected into the tube assumes a normal temperature in the order of 10° to 20° C., and thus present a temperature differential with respect to the temperature which is optimally suited to the determination. Hence, their injection cools down the tube so that the desired temperature of 37° C. cannot be reached for a considerable length of period at the commencement of the reaction between sample liquid and reagent. This cannot assure a reliable determination or analysis.

To avoid the foregoing problem, a chemical analyzer which heats the reagent and cleaning liquid to a given temperature before they are introduced into the reaction tube has been proposed. Such apparatus is illustrated in FIGS. 1 to 3. FIG. 1 shows a flow diagram. A liquid sample supply unit 101 includes a turntable 102, a plurality of sample tubes 103 disposed around the periphery thereof, and turntable drive 104. Liquid sample to be examined is contained in the individual sample tubes 103, and is withdrawn therefrom by sampling head 105 which comprises a suction tube 106 and an operator 107 which moves the suction tube.

The lower end of suction tube 106 is inserted into a sample tube which is held at a given position on the turntable 102, and sample liquid is withdrawn therefrom while it is maintained in this position. The suction tube can also be inserted into a cleaning vessel 108, as indicated in broken lines. When it is so inserted, water, for example, may be sprayed from nozzle 109 to clean the lower end of the suction tube. Sample liquid which has been withdrawn from the sample tubes 103 is introduced into a metering valve 110, which comprises a pair of stationary members 111, 112 and a rotating member 113 which is interposed therebetween in a manner to maintain a close contact therewith. The rotating member 113 is formed with at least two openings 114a, 114b which are of an equal volume. Stationary member 111 is connected with sampling head 105 while stationary member 112 is connected with directional control valve 115, which is in turn connected with pump 116. Pump 116 is connected with vessel 117, which contains a cleaning liquid, through valve 115. In the solid line position of valve 115, liquid sample to be examined is withdrawn from sample tube 103 by means of pump 116 and is introduced into the opening 114a formed in metering valve 110. In the broken line position of valve 115, cleaning liquid 118 contained within vessel 117 is withdrawn and is passed through metering valve 110 to be discharged into vessel 108, thus cleaning the internal passage of various parts to which the sample liquid may remain attached. Rotary reactor 119 comprises rotating body 120, and a plurality of reaction tubes 121 which are disposed on and held by rotating body 120 on a common circumference thereof. Rotating body 120 is intermittently driven for rotation by an associated drive. Characters $A_O, B_O, C_O \ldots L_O$ represent various positions where reaction tubes 121 remain stationary. Valves 145, 146 (see FIG. 2) are disposed on top of and beneath reactor 119. Rotating body 120 is centrally provided with light source 122, and detector 123 is disposed in opposing relationship therewith.

FIG. 2 shows the detail of reactor 119. In this Figure, a pair of vertically spaced partition plates 124, 125 define an air bath which maintains, by way of example, a constant temperature of 37° C. Pipe 126 extends through the plates and has its upper end secured to fixture 127 and its lower end to fixtures 128 and 129, whereby it is fixedly mounted on partition plates 124, 125. Collar 130 is fitted over pipe 126 in position thereon, and rotating body 120 is disposed around collar 130 and is rotatably supported by bearings 131, 132.

A plurality of reaction tubes 121 (twelve in the present example), are mounted on a common circle of rotating body 120. Individual reaction tubes are formed of a material such as fused quartz which exhibits a chemical resistance, and is made transparent in at least its region where light is intended to be passed therethrough. Light passages 133 are formed in rotating body 120 in the region of individual reaction tubes. An opening 134 is formed in a collar 130 and pipe 126 at a given position thereof so that light reflected by reflecting mirror 135, which is secured in the central portion of pipe 126, can be passed through opening 134 and passage 133 to irradiate a reaction tube 121. The transmitting light is detected by detector 123 which is disposed within shielded casing 136. Lamp protecting casing 139 is fixedly mounted on top of fixture 127 and contains lamp 122, condenser lens 137 and filter 138. Light from the lamp is collimated by the lens and is directed through pipe 126 onto reflecting mirror 135.

Rotating body 120 is peripherally formed with Geneva gear 140 having a number of teeth which is a multiple of the number of reaction tubes 121. In the present embodiment, it has 24 teeth. Geneva gear is intermittently engaged by pin 142 fixedly mounted on eccentric plate 141, which is fixedly mounted on shaft 143 that extends through and is supported by the upper partition plate 124. Gear 143a is secured to the upper end of the shaft and is operatively connected with drive 144 such as motor which is fixedly mounted on partition plate 124. By operating drive 144 in a programmed manner, it is possible to rotate Geneva gear by an amount corresponding to two teeth with one revolution of pin 142 about shaft 143, thus intermittently rotating body 120 and hence reaction tubes 121. Valves 145, 146 comprise stationary blocks 147, 149 and rotating blocks 148, 150. Stationary block 147 of upper valve 145 is secured to fixture 127 while rotating block 148 is fixedly mounted on rotating body 120 by means of holder 151. Stationary block 149 of lower valve 146 is secured to pipe 126 by means of holder 152 while its rotating block 150 is secured to the bottom of rotating body 120 by means of holder 153. Rotating blocks 148, 150 are formed with a number of flow passages 154, 155 which are equal in number to the number of reaction tubes 121 and which communicate with the latter through thin pipes 156. Those stationary blocks which are located at positions corresponding to the introduction and discharge or drain of sample, reagent, cleaning liquid or air are formed with passages 157, 158 which communicate through pipes 159, 159' with means which supply or drain liquid, introduce air or apply suction.

Returning to FIG. 1, position $A_O$ of reaction tube 121 represents a first position where sample and first reagent are introduced into a reaction tube. In this position, lower valve 146 of FIG. 2 is connected with stationary member 112 of liquid sample metering valve 110. Stationary member 111 of metering valve 110 is connected with line 161 which extends through preheater 160. Pump 162 is disposed in line 161, which has its lower end inserted into vessel 164 which is filled with first reagent 163.

The detailed construction of preheater 160 is shown in FIG. 3. As shown, preheater 160 represents an enclosed housing which is filled with liquid such as oil or water or gas. It internally houses heating element 166 which is connected with power source 165 for purpose of heating the liquid. Fan 167 is disposed in the bottom of the enclosed housing and is maintained in rotation by motor 168 to agitate the liquid contained in the interior of the housing to achieve a uniform temperature throughout the liquid. Temperature sensor 169 is located at a suitable position within the housing, and produces a temperature signal which is fed to control circuit 170 in order to control power source 165 so that the liquid temperature may be maintained substantially constant at 37° C., for example. Part of line 161 which is connected with metering valve 110 and pump 162 extends through the preheater housing, and is formed in zig-zag or helical form therein to enhance the thermal efficiency of heating the reagent to the given temperature. Lines 171 and 172 of a similar configuration as line 161 also extend through the preheater housing. Line 171 is used to supply second reagent while line 172 is used to supply cleaning liquid.

When pump 162 is set in motion, first reagent 163 is withdrawn, heated to the given temperature within preheater 160 and is introduced into metering valve 110. A fraction of sample liquid which is metered by the opening 114b of a given volume that is formed in rotating member 13 is displaced therefrom and fed through pipe 159' and lower valve 146 into the reaction tube 121 which is located at the position $A_O$. Means for agitating the sample and first reagent is located intermediate the positions $A_O$ and $B_O$. Specifically, in such a region, lower valve 146 is connected through pipe 159' with resistive tube 173 while upper valve 145 is connected with vacuum pump 176 through pipe 159, line 174 and reservoir 175. The top region of the reaction tube is reduced in pressure while air or any other desired gas is introduced into the bottom region thereof through tube 173. Air bubbles through the liquid upwardly, whereby the sample liquid and first reagent which have been introduced into the reaction tube at position $A_O$ are sufficiently agitated to accelerate the reaction therebetween.

Position $H_O$ represents the reaction tube position where the second reagent is introduced. At this position, lower valve 146 is connected through pipe 159' and line 171 with pump 177, and has its end inserted into vessel 179 which is filled with second reagent 178. The operation of a pump 177 withdraws second reagent, which is then heated to a given temperature by passing through preheater 160, and thereafter introduced into a corresponding reaction tube 121 through lower valve 146. Agitation means is similarly disposed intermediate positions $H_O$ and $I_O$. Air is introduced through resistive tube 180 and lower valve 146 to produce bubbles which achieves an agitation of second reagent with the sample which has terminated the reaction with or is in the process of reaction with first reagent. Position $J_O$ represents a determining position where light from lamp 122 is passed through the correspondingly located reaction tube to irradiate the reaction solution and the resulting transmitting light is detected by detector 123. An output signal from the detector is applied to amplifier 181 and thence to a recorder or display 182, thus plotting the light absorbance against the time axis. Part of the output signal from amplifier 181 is also fed to A-D converter 183 to be converted into a digital signal, which may be fed to data analyzer 184 such as an electronic computer, for example, to effect a desired calculation. The calculated result, for example, the enzyme activity is displayed after each determination or in a desired manner.

Positions $K_O$ and $L_O$ each represent a cleaning position where a cleaning liquid such as water which is heated to a given temperature is introduced through lower valve 146, pipe 159' and line 172. Line 172 is connected with vessel 117 through air mixer 185 and pump 186. Compressed air is supplied from compressor 187 to air mixer 185 through valve 188 to admix air with cleaning liquid supplied from pump 186. As a consequence, cleaning liquid which contains bubbles is introduced into reaction tube 121, thus enhancing the cleaning effect. Between positions $J_O$ and $K_O$, between positions $K_O$ and $L_O$ and between positions $L_O$ and $A_O$ where the liquid content within a reaction tube is to be discharged or drained, compressed air is introduced into the top of the reaction tube from compressor 187 through valve 189, line 190, pipe 159 and upper valve 145, thus pneumatically displacing the liquid from the reaction tube through lower valve 146, pipe 159' and line 191 and thence to a drainage sump (not shown).

With the described arrangement, reagent is heated within preheater 160 to a temperature which is substantially the same as that of the reactor before it is fed into reaction tubes, so that the reaction solution is maintained at a given temperature during the reaction and during the determination, thus permitting an accurate colorimetric determination.

However it will be understood that the resulting arrangement is complicated and bulky in size since the air bath defined by partition plates 124, 125, and which maintains a constant temperature therein, must house a number of parts including rotating body 120, reaction tubes 121 fixedly mounted thereon, valves 145, 146 which supply sample liquid, first and second reagent and cleaning liquid into the reaction tubes, reflecting mirror 135, detector 123 and intermittent drive associated with rotating body 120. Because the reaction tubes are completely secured to the rotating body, it is difficult to replace them. Additionally, in the event of a failure of valves, they cannot be repaired without disassembling the arrangement. A more significant disadvantage is the fact that valves, reflecting mirror, detector and intermittent drive which need not be maintained at a constant temperature are also assembled into the air bath, thus requiring an increased and wasteful heat capacity of the air bath. It will be appreciated that the maintenance of a constant temperature is required only for the reaction tubes and various liquids which are injected therein while valves, reflecting mirror, detector and intermittent drive need not be maintained at a constant temperature. It is also appreciated that it is only necessary that the chemical reaction solution comprising a mixture of sample liquid to be examined and reagent or reagents be maintained at a given temperature (for example, 37° C.) at the colorimetric determining position to assure a proper chemical reaction, but need not be closely controlled to such temperature at other positions.

SUMMARY OF THE INVENTION

It is an object of the invention to provide an automatic chemical analyzer which avoids the described disadvantages of the prior art, by providing an arrangement in which only reaction tubes (each supported by an associated holder) are allowed to move through an annular channel formed in a thermostat liquid vessel. A first reagent and sample liquid to be examined are injected into the tube under this condition, followed by the introduction of a preheated second reagent.

In accordance with the invention, the reaction tubes, liquid sample to be examined, and reagents which are injected into the tubes are the only components which are heated to a given temperature by means of the thermostat liquid vessel. Other members such as intermittent drive, optical colorimetric determining instrument, and pipes and lines which are used to inject the liquid sample or reagent into the tubes are not heated, thus avoiding a wasteful heating. This permits an efficient operation of the apparatus with a minimized heat capacity, thus providing an economically advantageous arrangement.

The first reagent and liquid sample to be examined are heated during their movement through the annular channel of the thermostat liquid vessel. When a colorimetric determining position is reached after the introduction of a second preheated reagent, they are rapidly heated to a given temperature by an auxiliary heater. Only the second reagent and cleaning liquid which are previously heated to a given temperature, thus further reducing the waste of heat capacity.

Holders detachably mount reaction tubes on a rotating plate which conveys them. This facilitates a replacement of reaction tubes. In addition, nozzles and pipes which are used to supply reagents, sample liquid to be examined and cleaning liquid into the reaction tubes are also removably mounted, again facilitating their replacement without requiring a disassembly of the entire arrangement. An injection nozzle associated with the liquid sample to be examined can be cleaned by using a nozzle cleaning unit, and reaction tubes are cleaned using heated cleaning liquid, both contributing to enhancing the accuracy of results of the analysis and determination.

DESCRIPTION OF PREFERRED EMBODIMENT

Figure 1:
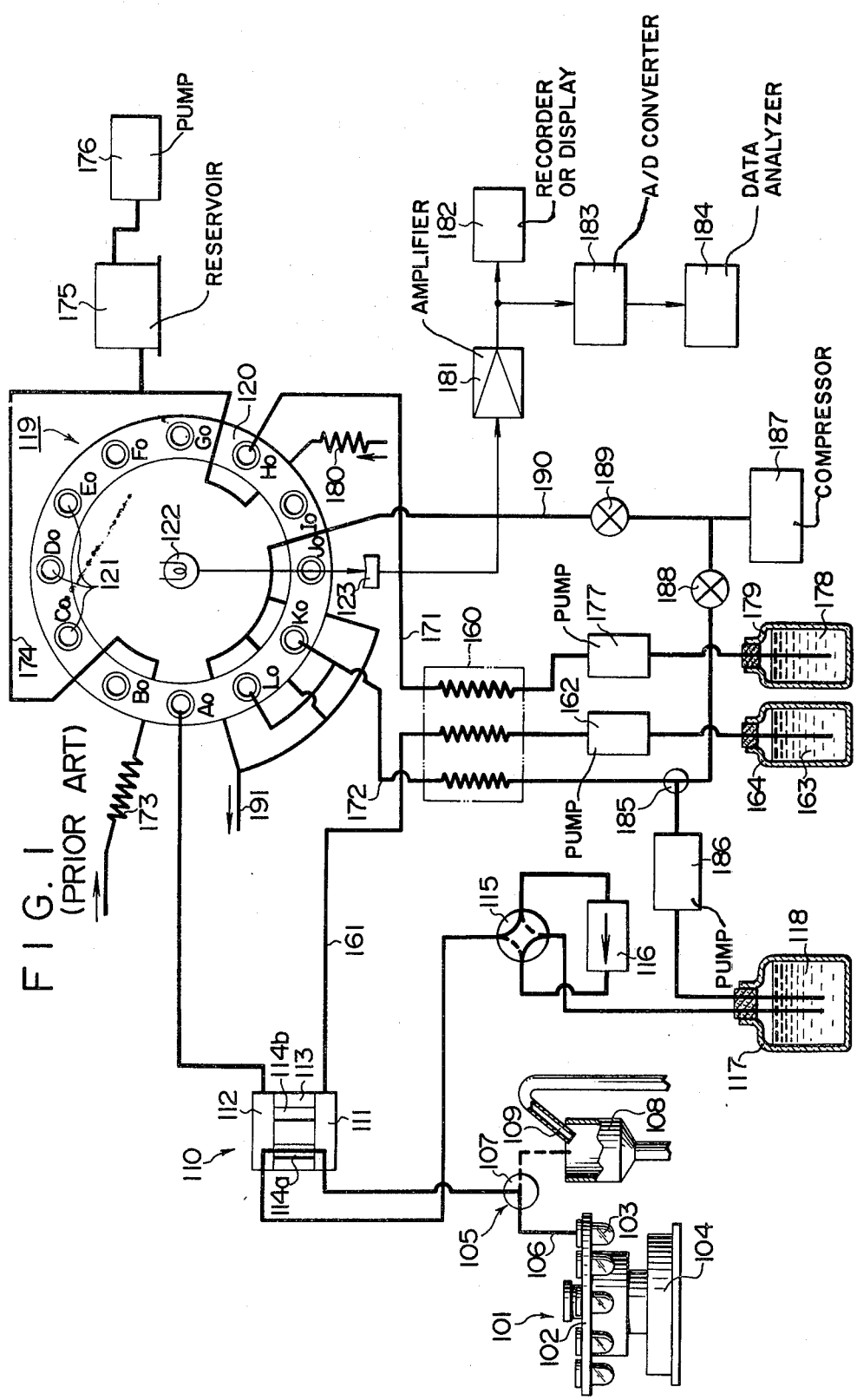
FIG. 1 is a schematic flow diagram of a conventional chemical analyzer.
Figure 2:
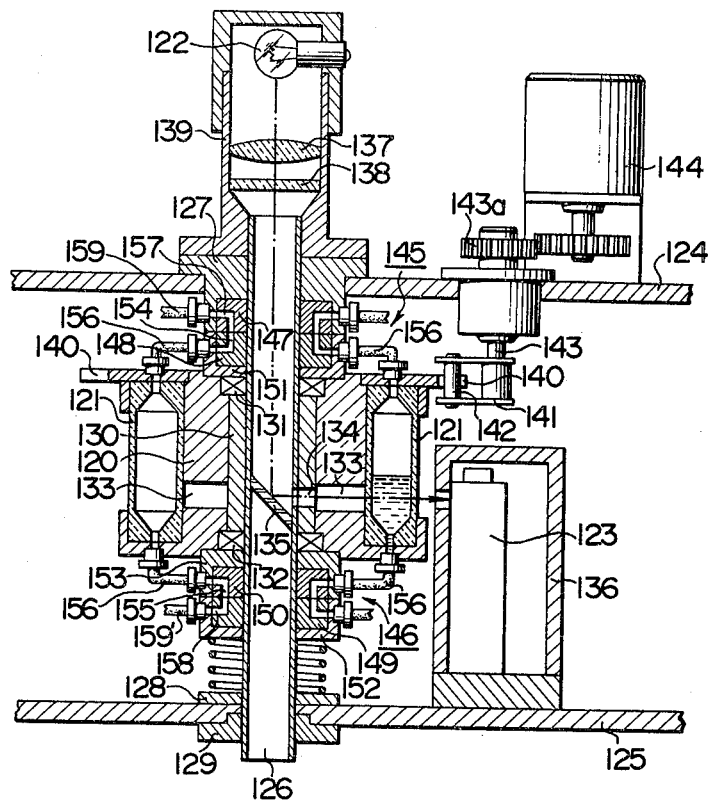
FIG. 2 is a cross section of rotating reactor used in the arrangement of FIG. 1.
Figure 3:
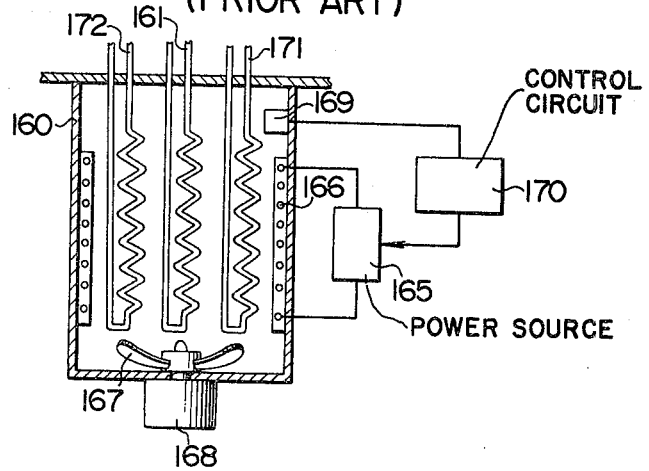
FIG. 3 is a cross section of preheater used in the arrangement of FIG. 1.
Figure 4:
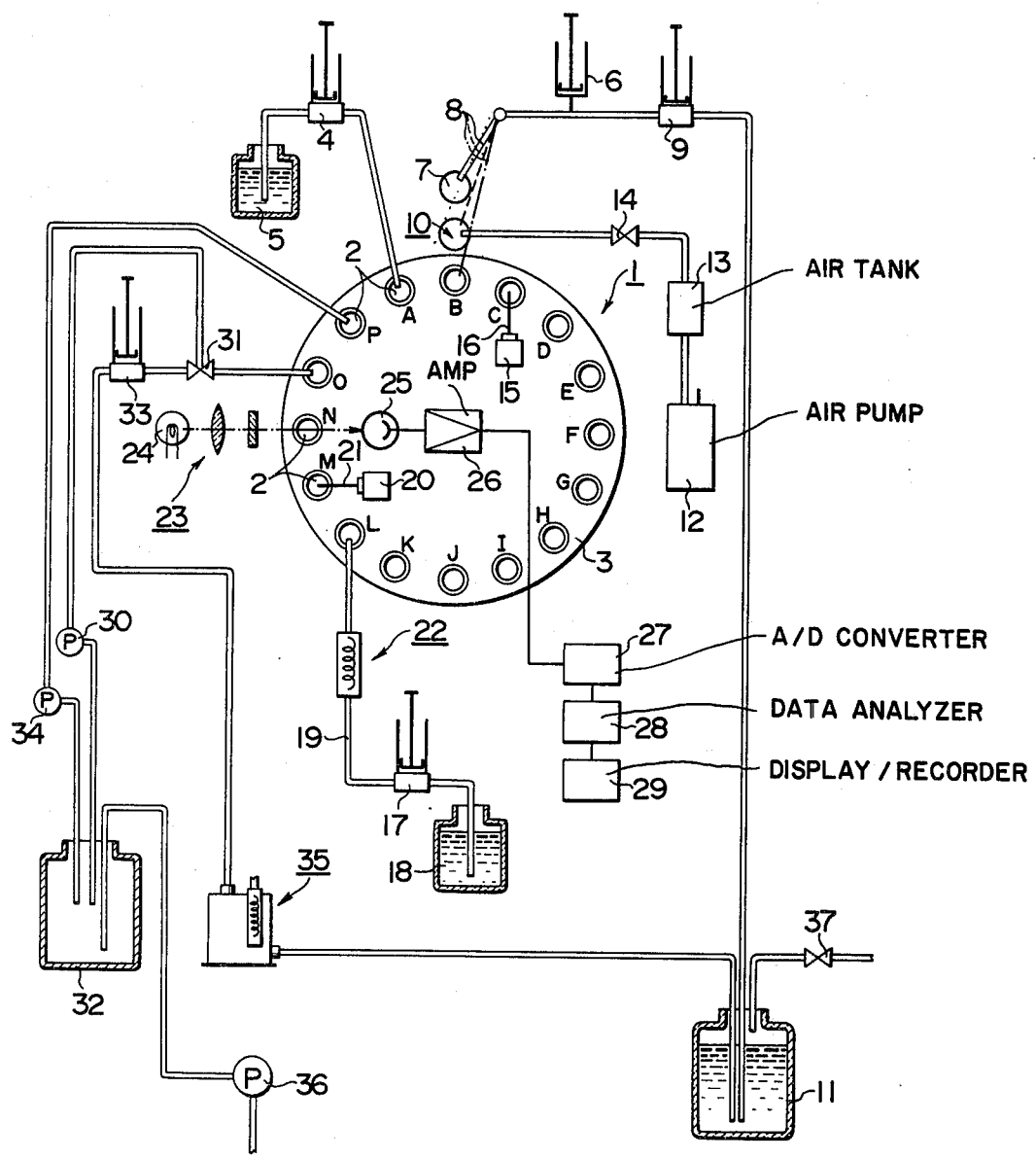
FIG. 4 is a schematic view and a flow diagram of an automatic chemical analyzer according to one embodiment of the invention.
Figure 5:
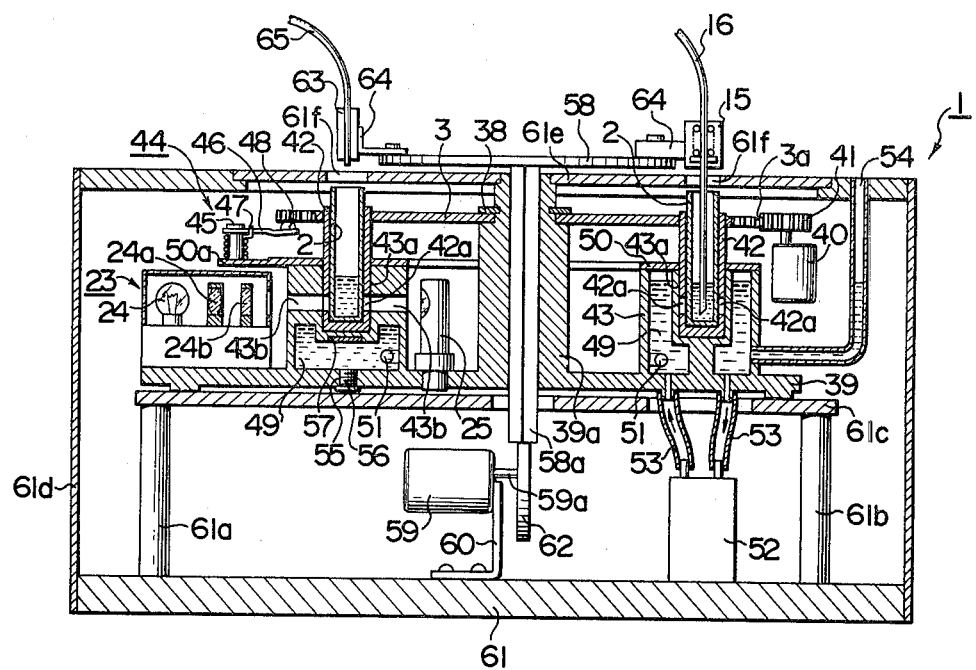
FIG. 5 is a cross section of a rotary reactor and a thermostat liquid vessel used in the apparatus of FIG. 4.

Referring now to FIGS. 4 and 5, there is shown a rotary reactor 1 constructed in accordance with the principles of the present invention. Reactor 1 includes a reaction tube conveying rotary disc 3 which is intermittently driven for rotation in one direction and which carries a plurality of reaction tubes 2 which are sequentially moved through and momentarily stopped at a first reagent injection position A, a liquid sample injection position B, a first agitation position C, a second reagent injection position L, a second agitation position M, a reaction solution determining position N, a reaction solution discharge or drain position O and a reaction tube cleaning position P. A plurality of reaction tube holders 42 (see FIG. 5) are disposed at equal intervals around a common circle of rotary disc 3 and depend therefrom. Each holder 42 has a light passing aperture 42a (see FIG. 5) formed in its sidewall. A plurality of reaction tubes 2 are fitted into and held by each holder 42. Each tube 2 is formed of a transparent material and holds a liquid sample to be examined. An annular thermostat liquid vessel 43 is disposed below the rotary disc 3 and is in vertical alignment with the holders 42. Each holder 42 is fitted in and moves through an annular channel 43a (see FIG. 5) in liquid vessel 43. Vessel 43 contains a quantity of thermostat liquid 49 which maintains the reaction solutions contained within reaction tubes 2 at a constant temperature. An auxiliary heater 57 (see FIG. 5) is disposed at reaction situation determining position N and is embedded in the wall of the vessel 43 which is close to the associated reaction tube for rapidly heating the reaction solution to a proper temperature. Openings 43b are formed in the wall of the vessel 43 at position N and communicates with the openings 42a formed in the holders 42 to permit light to pass therethrough. A ring-shaped heater 51 is disposed within vessel 43 for heating the liquid 49 to a given temperature. A circulation pump 52 is provided for circulating the liquid 49 within the vessel 43. An optical measuring instrument 23, including a light emitting unit and light receiving detector 25 disposed on the opposite sides of the openings 43b, are also provided.

In FIG. 4, characters A, B, C . . . P represent positions where reaction tubes 2 stop during an intermittent rotation of rotary disc 3. A variety of treatments are effected at each of these stop positions. First reagent injector 4 is disposed adjacent position A, and operates to withdraw a first reagent from reagent container 5 and to inject the reagent into the previously cleaned reaction tube 2 which has moved from position P to position A. Sample liquid injector 6 is disposed adjacent position B and operates to withdraw a liquid sample to be examined from sample container 7 through nozzle 8 and inject it through nozzle 8 into the reaction tube 2 which has moved to position B. Sample container 7 is mounted on a sample liquid supply unit (not shown) which is automatically supplied with a sample. After the injection, injector 6 has its nozzle 8 moved into a nozzle cleaning unit 10 wherein rinsing water withdrawn from water tank 11 by means of pump 9 is discharged through nozzle 8, thus cleaning both the interior and the exterior of nozzle 8. After the cleaning operation, compressed air is sprayed onto nozzle 8 from air pump 12 through air tank 13 and valve 14, thus drying the exterior of nozzle 8. It is to be noted that nozzle 8 is automatically returned to its initial position, namely, its position over sample container 7, when it is dried. Liquid contained within a reaction tube 2 which has moved to position C is subject to agitation by agitator 15 which includes agitating rod 16. Second reagent injector 17 is disposed adjacent position L, and withdraws a second reagent from reagent container 18 and injects it through transfer tube 19 into the reaction tube 2 which has moved to position L. Liquid contained within the reaction tube 2 which has moved to position M is subject to agitation by another agitator 20 including agitating rod 21. It is to be understood that the free end of transfer tube 19 has heater 22 attached thereto which heats the second reagent to a temperature which is substantially the same as the reaction temperature for enabling a reliable reaction result to be obtained.

Reaction solution contained within the reaction tube 2 which has moved to determining position N is subject to a colorimetric determination by means of optical measuring instrument 23 which is assembled into rotary reactor 1. Specifically, light from lamp 24 irradiates the reaction solution through the wall of the reaction tube 2 which has moved to position N, and the transmitting light is detected by detector 25, which feeds amplifier 26. The amplified signal is passed through A-D converter 27 and data analyzer 28 to be displayed and/or recorded by display/recorder 29.

At position O, reaction solution which has been subjected to the determination is withdrawn from reaction tube 2 by means of drain pump 39 to be drained through valve 31 into drainage tank 32. After the completion of the discharge of the reaction solution, rinsing water which is withdrawn from water tank 11 by means of rinse pump 33 is injected into the reaction tube located at position O through valve 31, thus cleaning it. When a reaction tube 2 moves to position P, rinsing water remaining therein is withdrawn by another drain pump 34 to be drained to drainage tank 32. It is to be noted that rinsing water heater 35 is interposed between tank 11 and pump 33 in order to maintain the rinsing water at a temperature which is 10° to 20° C. higher than the temperature at which the determination is made, thus preventing a fall in temperature of the tube. Drainage liquid within tank 32 is displaced therefrom by means of drain pump 36 to the outside the apparatus or the chamber while the supply of rinsing water to water tank 11 is controlled by valve 37.

Describing the general operation of the arrangement, injector 4 injects first reagent, withdrawn from reagent container 5, into the reaction tube 2 located at position A which is already cleaned and dried. Rotary disc 3 is then rotated clockwise to move tube 2 to position B where it is stopped. Injector 6 then inject liquid sample to be examined, which is withdrawn from sample container 7, into reaction tube 2 at position B through nozzle 8. Subsequently nozzle 8 is moved into cleaning unit 10 where pump 9 operates to supply rinsing water to it from water tank 11 and to open valve 14 to spray compressed air from tank 13 to dry the tube. The succeeding incremental clockwise rotation of rotary disc 3 brings the reaction tube 2 to position C where agitator 15 stirs liquid components within the tube to effect satisfactory reaction between first reagent and the sample. It is to be noted that during and after the reaction process, the solution within the reaction tube 2 is maintained at a given temperature by means of thermostat liquid vessel 43 (see FIG. 5). Subsequently, disc 3 is rotated clockwise to bring the reaction tube 2 to position L where injector 17 operates to inject second reagent from container 18 into the reaction tube 2. At this time, second reagent is heated by heater 22 before it is injected until it reaches substantially the same temperature as the reaction temperature, thus assuring a dependable achievement of intended reaction. When disc 3 is clockwise rotated to bring the reaction tube 2 to position M, agitator 20 stirs the reaction solution within the tube to permit a satisfactory reaction to occur between second reagent and the reaction solution. Then, disc 3 is rotated clockwise to bring the reaction tube 2 to position N where measuring instrument 23 effects a colorimetric determination, with the determination results being displayed and/or recorded by display/recorder 29. When disc 3 is rotated clockwise to bring the reaction tube 2 to position O, drain pump 30 operates to withdraw the reacted solution from within the reaction tube 2 through valve 31 and discharges it into waste tank 32. Subsequently, at this position O, rinse pump 33 operates to inject rinsing water from vessel 11 into the reaction tube 2. It is to be noted that at this time the rinsing water is heated, prior to the injection, by heater 35 to a temperature which is 10° to 20° C. higher than the temperature at which the determination is made, whereby a fall in temperature of the reaction tube 2 is effectively prevented. At position O, the injection and drainage of rinsing water into and out of the reaction tube 2 are repeated to enhance the rinsing effect. Disc 3 is then rotated clockwise to bring reaction tube 2 to position P where drain pump 34 completely withdraws the rinsing water which remains within the reaction tube 2, and discharges it into waste tank 32, thereby completely drying the reaction tube 2. When repeated discharge of rinsing water fills waste tank 32, the water may be discharged from tank 32 by means of discharge pump 36. Also, when the quantity of water which remains within water tank 11 is reduced, control valve 37 may be opened to replenish a fresh quantity of water. The last incremental rotation of disc 3 in the clockwise direction returns reaction tube 2 to its initial position A, thus completing a series of operations contemplated in the present embodiment. Other liquid samples to be examined may also be sequentially injected into other reaction tubes 2 which are carried by rotary disc 3, and may be successively analyzed by the described operations. When the number of liquid samples to be examined is increased, the same reaction tubes 2 may be repetitively used.

The construction of the above arrangement will now be described more specifically. FIG. 5 shows rotary reactor 1 which includes baseplate 61c mounted on stanchions 61a, 61b secured to basement 61 and located centrally within casing 61d. Receptacle member 39 is fixedly mounted on top of baseplate 61c, and is centrally formed with integral hollow stub shaft 39a having a relatively large wall thickness. A step is formed in the top of stub shaft or support member 39a, and rotary disc 3 is rotatably fitted over the top end of the shaft in abutment against the step. As a consequence, rotary disc 3 is concentric with stub shaft or support member 39a. Locking ring 38 is fitted over support member 39a to prevent its upward movement or withdrawal. Disc 3 is peripherally formed with gear 3a which is disposed for meshing engagement with a drive gear 41 that which is mounted on the output shaft of motor 40. In this manner, disc 3 can be rotated intermittently through an incremental angle in a given direction, which is clockwise as viewed in FIG. 4 in the present embodiment. Click stop means 44 is provided to stop disc 3 at a given position, and comprises click grooves, not shown, formed in the bottom surface of disc 3 around its outer periphery at a given interval, and stop claw 48 which is engageable with click groove to stop disc 3 at a given position. Claw 48 is mounted on an extension 50a of coverplate 50 of thermostat liquid vessel 43, which will be described later. Specifically, extension 5a has pin 45 on which arm 46 is pivotally conducted and has its free end connected with claw 48. Arm 46 is biased by spring 47 in a direction to prevent a rotation of disc 3.

A plurality of reaction tube holders 42 are disposed on a common circle of disc 3 at equal intervals around the periphery thereof and depend vertically therefrom. Each holder 42 is in the form of a hollow cylinder having a bottom for detachably supporting reaction tube 2. Light passing openings 42a extend diametrically through opposite portions of the sidewall of the lower portion of each holder 42 for allowing photometric light to pass through a reaction solution that is contained within transparent reaction tube 2 which is held within that holder 42.

Thermostat liquid vessel 43 having an annular configuration in plan view is disposed below disc 3 in alignment with holders 42, and is integrally formed with receptacle member 39. In its top portion, vessel 43 is formed with annular channel 43a intermediate its inner and outer peripheral walls so as to receive holders 42 therein and to permit an intermittent movement of holders 42 along the channel, together with reaction tubes 2 carried thereby. At a position which is aligned with the determining position N (see FIG. 4), the wall of vessel 43 is formed with openings 43b which communicate with openings 42a formed in a corresponding holder 42 so that openings 42a and 43b are aligned when a particular reaction tube 2 reaches the determining position N.

Vessel 43 contains a quantity of thermostat liquid 49 which is heated to and maintained at a given temperature by means of ring-shaped heater 51 disposed therein. Consequently, holders 42, reaction tubes 2 and sample liquid to be examined and first reagent which are injected into reaction tubes 2 are maintained at a given temperature. Liquid 49 is maintained in circulation by circulating pump 52 that communicates with vessel 43 through connection pipes 53, thus achieving a uniform temperature distribution throughout the entire body of thermostat liquid 49 contained within vessel 43. The top of vessel 43 is closed by coverplate 50, while its bottom is provided with drain port 55. Port 55 is normally blocked by plug 56. Liquid supply port 54 communicates with vessel 43.

At the determining position N, auxiliary heater 57 is embedded in the bottom wall of annular channel 43a for rapidly heating the reaction solution contained within reaction tube 2. The purpose of auxiliary heater 57 is to provide a further heating of the reaction solution contained in the tube which has been maintained at a given temperature by thermostat liquid 49, and to bring it to an optimum temperature for the determination within a reduced period of time. It is to be understood that heater 57 may be embedded in the sidewall rather than the bottom wall of annular channel 43a. In this manner, thermostat liquid vessel 43 is provided which fully utilizes the effectiveness of liquid heating and which eliminates adverse influences that may be caused by evaporation.

Optical measuring instrument 23 is disposed at the determining position N and on the opposite sides of openings 43b formed in the vessel wall. Instrument 23 includes light emitter and detector 25 disposed on receptacle member 39, both in alignment with openings 43b formed in the outer and inner walls of vessel 43. Light emitter comprises lamp 24, condenser lens 24a and filter 24b. Light from the emitter passes through outer openings 43b, opening 42a formed in the holder, reaction solution contained within reaction tube 2, the oppositely located opening 42a of the holder and inner opening 43b to impinge on detector 25.

Disc-shaped mounting plate 58 is disposed for free vertical movement above casing 61d which internally houses disc 3, tubes 2, holders 42, vessel 43, instrument 23 and the like. Mounting plate 58 is centrally mounted on the top end of shaft 58a which extends through the hollow shaft or support member 39a and through baseplate 61c and which has its lower end disposed in abutment against cam 62. Cam 62 is fixedly mounted on output shaft 59a of motor 59 that is secured over basement 61 by means of fixture 60. When motor 59 is driven, cam 62 causes a vertical movement of mounting plate 58 through shaft 58a. At given positions around the periphery thereof which correspond to the stop positions of rotary disc 3, mounting plate 58 has reagent injection nozzle holder 63, agitator 15 etc. mounted thereon by suitable means indicated at 64. While not shown in FIG. 5, another reagent injection nozzle holder, another agitator 50 and reagent heater 22 are similarly mounted on mounting plate 58, using suitable mounting means. Individual nozzles and agitating rods are disposed in opposing relationship with or extend into the top opening of reaction tubes 2 through openings 41f which are formed in top plate 61e of casing 61d. Movement of agitating rods 16, 21 and injection nozzles into and out of respective reaction tubes 2 takes place simultaneously when motor 59 is energized, thus simplifying the required construction. Reagent injection nozzle holder 63 is designed to be set in place by a simple insertion of injection nozzle 65. In agitators 15, 20, agitating rods 16, 21 are driven for rotation or oscillation by a drive from a motor or under pneumatic pressure.

It will be seen therefore that the rotary reactor 1 of the invention is capable of effecting reaction, photometric determination and cleaning operation while maintaining the reaction solution at an optimum temperature by means of the thermostat liquid vessel, thus assuring a high reliability of the analytical results.

Figure 6:
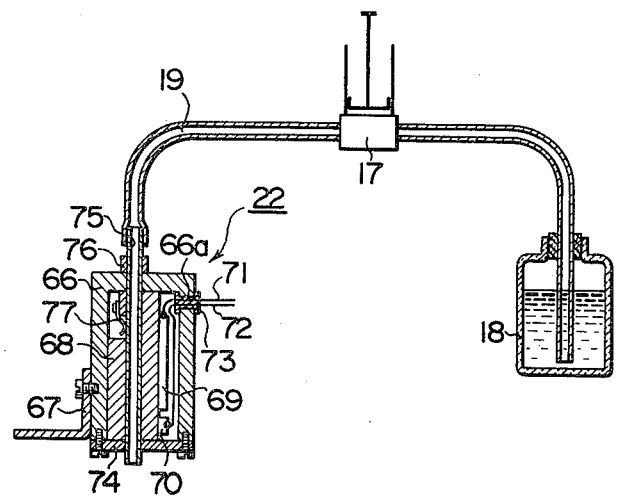
FIG. 6 is a schematic view, partly in section, of second reagent heater used in the arrangement of FIG. 4.

FIG. 6 shows the second reagent heater 22. It comprises heat insulating casing 66 that is secured to mounting plate 58 (see FIG. 5) by suitable means indicated at 67, metallic reagent heating body 68 of a high thermal conductivity and received within casing 66, heating element 69 attached to body 68, temperature sensor 70 connected with the heating body for detecting the temperature thereof, and heat insulating plate 74 which closes the bottom of casing 66. The sensor 70 operates to maintain the heating body at a temperature at which the determination is made. Reaction injection nozzle 75 extends through casing 66, body 68 and insulating plate 74. Stop 76 is secured toward the upper end of nozzle 75, and leaf spring 77 is connected with heating body 68 and cooperates with the stop to maintain nozzle 75 at a given position. Lead wires 71, 72 associated with heater 69 and sensor 70 are taken out of casing 66 through bushing 73 which is fitted into opening 66a formed in casing 66. The top end of nozzle 75 is connected with transfer tube 19. It is to be noted that nozzle 75 has a capacity which exceeds that which is required by one sample.

When injector 17 withdraws second reagent from container 18 and fills nozzle 75 with the reagent, the latter is heated to and maintained at a given temperature before a required fraction thereof is injected into reaction tube 2. Since reagent heater 22 is entirely formed as a heat insulating, enclosed structure, the heating can be achieved to a high accuracy and with a high efficiency. Since the heated area is located at the free end of transfer tube 19 or nozzle 15 which is located most close to reaction tube 2, a temperature fall during the injection of the reagent is avoided, maintaining the reaction solution at a given temperature. The construction of the entire unit is simplified inasmuch as it is only necessary to heat nozzle 75. Nozzle 75 can be simply mounted in place or removed by a mere insertion or withdrawal thereof, thus greatly facilitating a replacement of nozzle used. By moving fixing means 67, unit 22 can be mounted anywhere desired.

Figure 7:
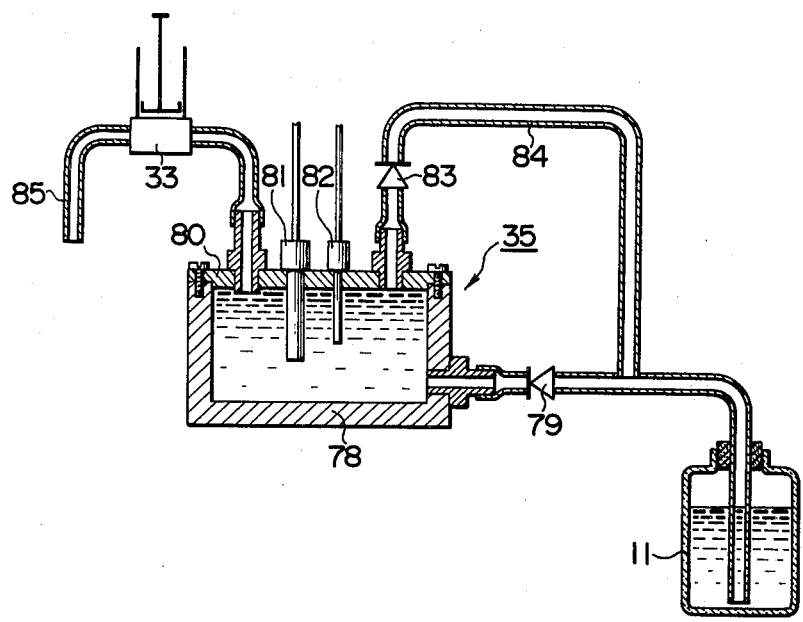
FIG. 7 is a schematic view, partly in section, of a rinse water heater used in the arrangement of FIG. 4.

FIG. 7 shows rinse water heater 35. It comprises a heat insulating vessel 78 formed of a highly heat insulating material and which is connected with water tank 11 through check valve 79, a cover 80 formed of a highly heat conductive material and which closes vessel 78, heater 81 which heats the rinse water contained in the vessel, temperature sensor 82 mounted in cover 80, relief valve 83 having its one end connected with an opening formed in cover 80 and its other end connected with water tank 11 through transfer tube 84, and another transfer tube 85 having its one end connected with an opening formed in cover 80 through rinse pump 33 and its other end connected with rinse water injection nozzle, not shown. Sensor 82 operates to control the temperature of rinse water contained within vessel 78 to be 10° to 20° C. higher than the temperature at which the determination is made so that a temperature fall during the transfer results in the temperature of rinse water being injected into reaction tube 2 which is substantially comparable to the temperature being contemplated for the determination. When the pressure within vessel 78 rises excessively, relief valve 83 opens to return part of the rinse water to water vessel 11, thus reducing the pressure and maintaining it at a constant value. In operation, rinse water is withdrawn by pump 33 from water tank 11 and supplied to vessel 78, where it is heated before injection into reaction tube 2. The provision of relief valve 83 enhances the safety of heater 35. The safety is also ensured by the highly thermally conductive material which forms cover 80 and which transfers the heat from heater 81 to sensor 82 to cause a temperature control in the event rinse water is completely discharged from vessel 78.

Figure 8:
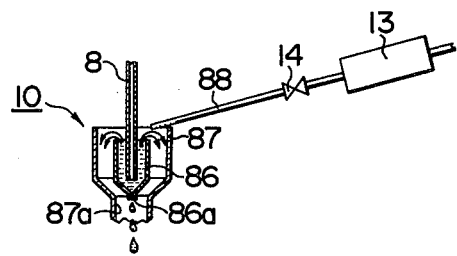
FIG. 8 is a schematic view of a nozzle cleaning unit associated with a liquid sample injector.

FIG. 8 shows nozzle cleaning unit 10 which cleans the nozzle of sample liquid injector. Unit 10 comprises hollow cylindrical body 86 having drain port 86a formed in its bottom, receiver 87 disposed so as to surround cylindrical body 86 and having drain port 87a formed in its bottom which is connected with the drainage tank, and air injection nozzle 88 having its free end disposed adjacent to nozzle 8 and its opposite end connected with air tank 13 through valve 14.

In use, nozzle 8 is brought down to a suitable position within cylindrical body 86, and pump 9 (see FIG. 4) is operated to flow rinse water through nozzle 8. The flow of rinse water cleans the interior of nozzle 8, and is discharged through port 86a of cylindrical body 86. By feeding a quantity of rinse water into nozzle 8 which exceeds the discharge capability of port 86a, there occurs an overflow over the upper edge of the cylindrical body 86, thus cleaning the exterior of nozzle 8. Rinse water from either flow path accumulates in receiver 87 and is discharged to the drainage tank through port 87a. Subsequently, compressed air from air tank 13 is injected from nozzle 88 by opening valve 14, while raising nozzle 8 upwardly from cylindrical body 86, thus drying the exterior of nozzle 8. Any splashes of rinse water which are driven off nozzle 8 at this time are also collected by receiver 87 to be drained to the drainage tank. In this manner, the cleaning of the interior and the exterior of nozzle 8 as well as drying thereof can be rapidly and satisfactorily achieved with unit 10.

What is claimed is:
1. An automatic chemical analyzer comprising:
a reaction tube conveying rotary disc having a plurality of reaction tube holders disposed at equal intervals along a circle thereof;
means for intermittently rotating said rotary disc in a single direction such that each of said reaction tube holders are sequentially stepped through a plurality of positions including a first reagent injection position, a sample injection position where a liquid sample to be examined is injected, a first agitating position, a second reagent injection position, a second agitating position, a reaction solution determining position, a reaction solution drain position and a reaction tube cleaning position;
each of said reaction tube holders depending from said rotary disc and having light passing openings formed in its sidewall;
a plurality of reaction tubes equal in number to the number of said reaction tube holders and formed of a transparent material, each of said reaction tubes being disposed in a respective said holder;
a thermostat liquid vessel having an annular configuration in plan view and disposed below said rotary disc in alignment with the reaction tube holders in such a manner that said holders are disposed in and move through a thermostat liquid located in said liquid vessel;
means for maintaining said thermostat liquid at a constant temperature;
an auxiliary heater embedded in the wall of said thermostat liquid vessel at said determining position and close to the location of a reaction tube located at said determining position;
openings formed in opposite walls of said thermostat liquid vessel at said determining position, said openings in said wall of said vessel communicating with the openings formed in said holders;
a circulation pump for circulating said thermostat liquid through said vessel;
an optical measuring instrument including a light emitter and light receiving detector which are disposed on opposite sides of said openings formed in said vessel walls;

a first reagent injector for withdrawing a first reagent from a reagent container and injecting it into a reaction tube located at said first reagent injection position;

a sample liquid injector for withdrawing a sample liquid from a sample container and injecting it into a reaction tube located at said sample injection position;

a first agitator for agitating and mixing said first reagent and said sample liquid contained within a reaction tube located at said first agitating position;

a second reagent injector for withdrawing a second reagent from a reagent container and injecting it into a reaction tube located at said second reagent injection position through a reagent heater;

a second agitator for agitating and mixing said first reagent, said sample liquid and said second reagent which is contained in a reaction tube located at said second agitating position;

a drain pump for draining the reacted reaction solution from a reaction tube located at said reaction solution drain position into a drainage tank;

a rinse pump for injecting a heated rinse water into a reaction tube located at said drain position after said reaction solution has been drained therefrom, thus cleaning the interior of said tube; and another drain pump for draining a rinse water from within a reaction tube located at said reaction tube cleaning position to a drainage tank.

2. An automatic chemical analyzer according to claim 1 in which said auxiliary heater is embedded in the bottom wall of said annular channel at a position corresponding to said determining position.

3. An automatic chemical analyzer according to claim 1 in which said openings formed in said holders to permit light to pass therethrough are located at diametrically symmetrical positions in the sidewall of said holder to enable the light to transmit through the reaction solution contained in said reaction tube in the horizontal direction.

4. An automatic chemical analyzer according to claim 1 in which said circulation pump is connected with the thermostat liquid vessel through pipes and causes a circulation of the thermostat liquid therein to maintain a uniform temperature distribution thereof throughout the vessel.

5. An automatic chemical analyzer according to claim 1 in which said light emitter of said optical measuring instrument comprises a lamp, a condenser lens and a filter.

6. An automatic chemical analyzer according to claim 1 in which said liquid sample injector includes a nozzle that is used to withdraw or discharge said liquid sample to be examined, said nozzle being moved to a nozzle cleaning unit to be cleaned thereby after it has injected said liquid sample into one of said reaction tubes.

7. An automatic chemical analyzer according to claim 6 in which said nozzle cleaning unit includes a hollow cylindrical body formed with a drain port in its bottom for cleaning the exterior of the nozzle, a rinse pump for supplying and forcing a rinse water into said nozzle which is located within said nozzle, a receiver disposed in surrounding relationship around said cylindrical body for receiving used water, and an injection nozzle which sprays compressed air around said cleaned nozzle, thereby drying it.

8. An automatic chemical analyzer according to claim 1 in which said second reagent heater comprises a metallic heating body having a high thermal conductivity and received within a heat insulating casing, a reagent injection nozzle disposed to extend through the heating body, a heating element for heating the heating body, and a temperature regulator which detects the temperature of the heating body and maintains the latter at a temperature at which the determination is made.

9. An automatic chemical analyzer according to claim 8 in which said reagent injection nozzle is detachably mounted on said heating body and secured in place by means of a stop fixedly attached to the nozzle and a leaf spring that is mounted on the heating body, the free end of said nozzle extending beyond said reagent heater.

10. An automatic chemical analyzer according to claim 1 in which said rinse water heater comprises a heat insulating vessel connected with a water tank through a check valve, a heating element to heat rinse water contained in said vessel, a temperature regulator which senses the temperature of said rinse water and maintains the latter at a temperature which is 10° to 20° C. higher than the temperature of said reaction solution at which the determination is made, and a relief valve which is responsive to a high pressure occurring in said vessel to reduce the pressure by returning part of said rinse water to said water tank, thus maintaining a constant pressure within said vessel.

11. An automatic chemical analyzer according to claim 1 in which said auxiliary heater is embedded in the side wall of said annular channel at a position corresponding to said determining position.

* * * * *